(12) United States Patent
Farrugia et al.

(10) Patent No.: US 6,517,517 B1
(45) Date of Patent: Feb. 11, 2003

(54) AUTOMATED INJECTION DEVICE FOR ADMINISTRATION OF LIQUID MEDICAMENT

(75) Inventors: Gianrico Farrugia, Rochester, MN (US); Mark H. Ereth, Rochester, MN (US); William W. Brooks, Jr., Rochester, MN (US); Jerry Neubauer, Stewartville, MN (US); Jim Rigotti, Rochester, MN (US); Peter Schuller, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 151 days.

(21) Appl. No.: 09/589,962

(22) Filed: Jun. 8, 2000

(51) Int. Cl.[7] .............................................. A61M 37/00
(52) U.S. Cl. ........................ 604/131; 604/138; 604/204; 604/212
(58) Field of Search ................................ 604/131, 133, 604/134, 135, 136, 137, 138, 200, 203, 204, 212, 244

(56) References Cited

U.S. PATENT DOCUMENTS

| | | | |
|---|---|---|---|
| 3,094,989 A | 6/1963 | Stauffer | |
| 4,031,893 A | 6/1977 | Kaplan et al. | |
| 4,178,928 A | 12/1979 | Tischlinger | |
| 4,226,235 A | 10/1980 | Sarnoff et al. | |
| 4,227,528 A | 10/1980 | Wardlaw | |
| 4,378,015 A | * 3/1983 | Wardlaw | .................... 604/137 |
| 4,394,863 A | 7/1983 | Bartner | |
| 4,447,231 A | 5/1984 | Bekkering | |
| 4,484,910 A | 11/1984 | Sarnoff et al. | |
| 4,487,602 A | * 12/1984 | Christensen et al. | ........ 604/137 |
| 4,512,767 A | * 4/1985 | Denance | .................... 604/137 |
| 4,529,403 A | 7/1985 | Kamstra | |

(List continued on next page.)

FOREIGN PATENT DOCUMENTS

| | | |
|---|---|---|
| WO | WO 00/13725 | 3/2000 |
| WO | WO 00/29047 | 5/2000 |
| WO | WO 00/32258 | 6/2000 |

*Primary Examiner*—Teresa Walberg
*Assistant Examiner*—Fadi H. Dahbour
(74) *Attorney, Agent, or Firm*—Fush & Richardson, P.C., P.A.

(57) ABSTRACT

An automated injection device for administration of one or more liquid medicaments that is particularly useful for self-administration of liquid medicaments such as those used to treat anaphylactic shock, heart attack, exposure to toxic agents, or other conditions may include a number of features designed to reduce both the size and complexity of the device. With reduced size, the device may provide greater convenience and portability. Importantly, the reduced size may encourage more users to carry the device, and thereby reduce the risks associated with the conditions mentioned above. With reduced complexity, the device can be constructed at a lower cost. Moreover, the device can be more reliable and simple to operate.

47 Claims, 6 Drawing Sheets

U.S. PATENT DOCUMENTS

| | | |
|---|---|---|
| 4,565,543 A | 1/1986 | Bekkering et al. |
| 4,573,971 A | 3/1986 | Kamstra |
| 4,624,660 A | 11/1986 | Mijers et al. |
| 4,640,686 A | 2/1987 | Dalling et al. |
| 4,661,098 A | 4/1987 | Bekkering et al. |
| 4,678,461 A | 7/1987 | Mesa |
| 4,795,433 A | 1/1989 | Sarnoff |
| 4,822,340 A | 4/1989 | Kamstra |
| 4,832,682 A * | 5/1989 | Sarnoff ........................ 604/137 |
| 5,085,642 A | 2/1992 | Sarnoff et al. |
| 5,092,843 A * | 3/1992 | Monroe et al. ............. 604/138 |
| 5,102,393 A | 4/1992 | Sarnoff et al. |
| 5,114,406 A | 5/1992 | Gabriel et al. |
| 5,137,516 A * | 8/1992 | Rand et al. .................. 604/136 |
| 5,167,632 A | 12/1992 | Eid et al. |
| 5,320,609 A * | 6/1994 | Haber et al. ................. 604/135 |
| 5,354,286 A | 10/1994 | Mesa et al. |
| 5,405,362 A | 4/1995 | Kramer et al. |
| 5,451,210 A * | 9/1995 | Kramer et al. .............. 604/137 |
| 5,478,316 A | 12/1995 | Bitdinger et al. |
| 5,632,730 A * | 5/1997 | Reinert ........................ 604/137 |
| 5,822,715 A | 10/1998 | Worthington et al. |
| 5,980,491 A * | 11/1999 | Hansen ........................ 604/137 |
| 6,149,626 A * | 11/2000 | Bachynsky et al. ......... 604/134 |

* cited by examiner

AUTOMATED INJECTION DEVICE FOR ADMINISTRATION OF LIQUID MEDICAMENT

TECHNICAL FIELD

This invention relates to automated injection devices for administration of liquid medicaments.

BACKGROUND

Automated injection devices enable patients to administer a dosage of liquid medicament for therapeutic purposes. An automated injection device may contain, for example, one or more liquid medicaments effective in treating anaphylactic shock caused by severe allergic reactions to foods, insect stings, and the like. An example of a liquid medicament suitable for treatment of anaphylactic shock is epinephrine. Automated injection devices that carry epinephrine are sometimes referred to as "EPI" injectors. Other types of injection devices may carry antiarrhythmic medicaments for administration during a heart attack, as well as antidotes to a variety of toxic agents, e.g., for military applications.

Most automated injection devices of this type are designed for single use in an emergency situation. For this reason, extended longevity usually is a requirement. In particular, such devices typically are constructed to contain a measured dosage of the liquid medicament in a sealed and sterile environment over an extended period of nonuse. The devices are designed for quick administration of the liquid medicament, often under the stress of shock. In many devices, a spring-loaded actuator facilitates automated injection without the need for significant manual intervention by the patient. The patient merely actuates a trigger that releases the spring-loaded actuator. The actuator drives a needle into the patient's skin and quickly releases the liquid medicament. In this manner, there is no need for the patient to manually pierce the skin or operate a syringe for delivery of the liquid medicament. Often, the needle is not even visible to the patient.

The unpredictability of anaphylactic shock, heart attack, and other emergency medical conditions requires that the patient carry the automated injection device at all times. Unfortunately, the size and weight of many automated injection devices makes them cumbersome and inconvenient to carry. A number of carrying cases, holsters, belts, and the like have been devised to enhance the portability of automated injection devices. Still, the inconvenience associated with many devices causes users to disregard medical risks, and simply leave the automated injection devices at home. This is particularly the case for users engaged in active lifestyles involving high levels of physical activity.

SUMMARY

The present invention is directed to automated injection devices for administration of one or more liquid medicaments, and methods for their use. A device in accordance with the present invention may be particularly useful for self-administration of liquid medicaments such as those used to treat anaphylactic shock, heart attack, exposure to toxic agents, or other emergency medical conditions.

A device in accordance with the present invention may include a number of features designed to reduce both the size and complexity of the device. With reduced size, the device may provide greater convenience and portability. Importantly, the reduced size may encourage more users to carry the device, and thereby reduce the risks associated with the medical conditions mentioned above.

With reduced complexity, the device can be constructed at a lower cost. Moreover, the device can be more reliable and simple to operate. In some embodiments, the device can be made from recycled and recyclable materials, reducing waste following use. The device preferably is made water-resistant to promote longevity and durability to environmental conditions. Also, in some embodiments, the device may be suitable for administration of liquid medicaments on a non-emergency basis, e.g., to administer insulin to diabetic patients.

In one embodiment, the present invention provides an automated injection device comprising a reservoir, a needle in fluid communication with the reservoir, a piston member with a piston face positioned within the reservoir, a spring adjacent the piston member, and a loading member that is movable to compress the spring, the loading member permitting the spring to expand following compression, whereby the expanding spring drives the piston member such that the piston face moves within the reservoir and expels the contents of the reservoir through the needle.

In another embodiment, the present invention provides an automated injection device comprising a housing having a first end and a second end, the housing defining an opening at the second end, a piston member slidably mounted within the housing, a reservoir slidably mounted within the piston member, a needle in fluid communication with the reservoir, a piston mounted within the piston member with a piston face positioned within the reservoir, a spring that bears against the piston member on a side of the piston member adjacent the first end of the housing, and a loading member oriented to drive the piston member toward the first end of the housing and thereby compress the spring, wherein the piston member and the loading member are configured to permit relative movement of the piston member and the loading member following compression of the spring, and the loading member defines a stop member that limits travel of the reservoir toward the second end of the chamber, whereby the spring drives the piston member relative to the loading member and toward the second end of the housing, and the piston member drives the reservoir against the stop member such that continued movement of the piston member relative to the reservoir drives the piston face through the reservoir and expels the contents of the reservoir through the needle.

In an added embodiment, the present invention provides a method for injection of a liquid medicament using a device having a reservoir, a needle in fluid communication with the reservoir, a piston member with a piston face positioned within the reservoir, a spring that bears against the piston member, and a loading member oriented to drive the piston member to compress the spring, the piston member and the loading member being configured to permit relative movement when the compressed spring reaches a sufficient level of spring force, wherein a portion of the loading member extends outward from the device, the method comprising pushing the loading member against a patient to drive the loading member into the device and toward the piston member, thereby compressing the spring, wherein the spring expands to drive the piston member relative to the loading member and extend the needle outward from the device and drive the piston face to expel the contents of the reservoir through the needle.

In a further embodiment, the present invention provides a method for injection of a liquid medicament using a device having a housing having a first end and a second end, the housing defining an opening at the second end, a piston member slidably mounted within the housing, a reservoir slidably mounted within the piston member, a needle in fluid communication with the reservoir, a piston mounted within the piston member with a piston face positioned within the reservoir, a spring that bears against the piston member on a side of the piston member adjacent the first end of the housing, and a loading member oriented to drive the piston member toward the first end of the housing and thereby compress the spring, wherein the piston member and the loading member are configured to permit relative movement when the compressed spring reaches a sufficient level of spring force, the loading member defines a stop member that limits travel of the reservoir toward the second end of the chamber, and a portion of the loading member extends outward from the opening, the method comprising pushing the loading member against a patient to drive the loading member into the device and toward the piston member, thereby compressing the spring, wherein the spring expands to drive the piston member relative to the loading member and extend the needle outward from the opening and drive the piston face to expel the contents of the reservoir through the needle.

In another embodiment, the present invention provides an automated injection device comprising a reservoir, a needle in fluid communication with the reservoir, a piston member with a piston face positioned within the reservoir, a spring adjacent the piston member, and a loading member that is movable to compress the spring and permit the spring to expand following compression, the expanding spring driving the piston member such that the piston face moves within the reservoir and expels the contents of the reservoir through the needle, wherein the piston member and the reservoir partially overlap along a longitudinal extent of the device and are sized such that the device has a length of less than or equal to approximately 3.0 inches and a width of less than or equal to approximately 2.0 inches.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
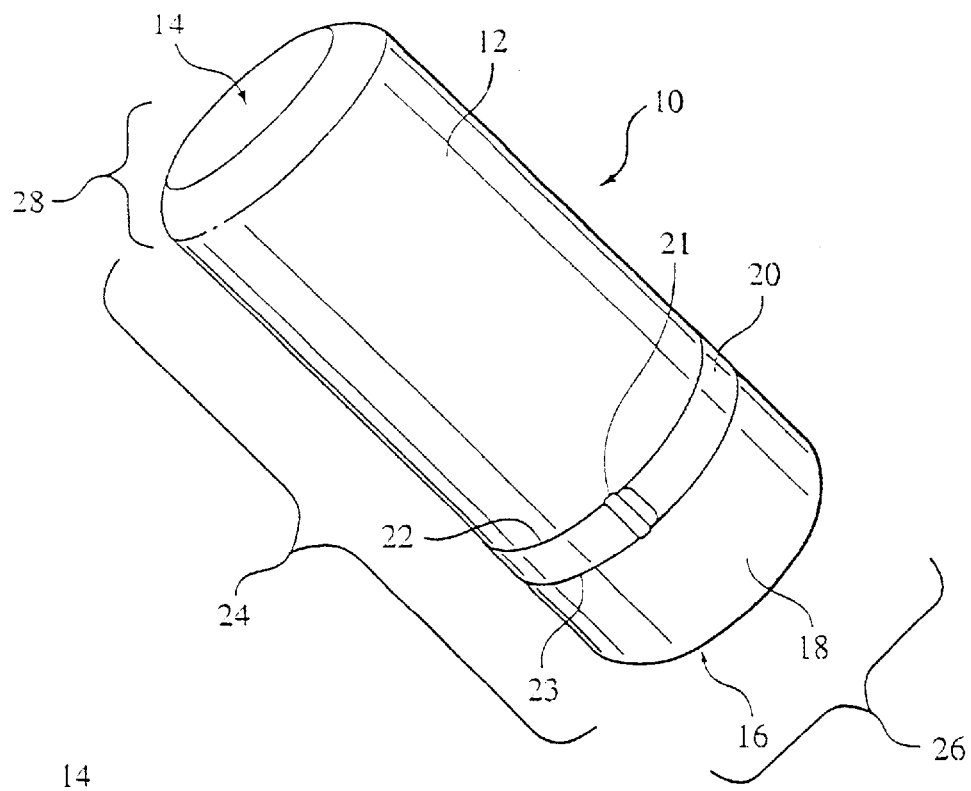
FIG. 1 is a perspective exterior view of an automated injection device in accordance with an embodiment of the present invention.

FIG. 1 is a perspective exterior view of an automated injection device 10 in accordance with an embodiment of the present invention. As shown in FIG. 1, device 10 may include a housing 12 having a proximal end 14, a distal end 16, and a cap 18 mounted at the distal end. Housing 12 contains appropriate components for containment and automated delivery of liquid medicaments for injection to a user. Cap 18 protects distal end 16, which forms the operative end of device 10, when the device is not in use.

The user removes cap 14 prior to use. In the example of FIG. 1, cap 18 may include a tear-away strip 20 that couples the cap to housing 12 at distal end 16. Strip 20 may be similar to the strips commonly used with caps for plastic milk cartons and the like, and provides a tab 21 for grasping by the user. Cap 18 and strip 20 may be integrally molded from plastic and coupled to the cap and housing 12 with a pair of thinned, scribed, or perforated joints 22, 23 that extend circumferentially about distal end 16 and promote tearing of the strip from the cap. Upon removal of strip 20, cap 18 is easily removable to expose distal end 16.

With further reference to FIG. 1, housing 12 may be slightly elongated, providing a length 24 that exceeds a width 26 and depth 28 of device 10. In some embodiments, width 26 and depth 28 may be equivalent, particularly if device 10 has a substantially cylindrical shape and circular cross-section. Housing 12 is susceptible to a number of different shapes and sizes. In general, housing 12 is constructed such that device 10 assumes a shape and size appropriate for convenient portability, e.g., in the shirt or pants pocket of the user. In some embodiments, as will be described, housing 12 may be constructed as a keychain fob and provided with appropriate coupling hardware for mounting on a keyring or for receipt of keys.

In other embodiments, housing 12 can be constructed for convenient storage in a portable holster, belt, or case, or for attachment to other portable devices such as mobile telephones, personal digital assistants (PDA's), and the like. In each embodiment, however, housing 12 preferably is constructed with reduced size and portability as one of the primary design objectives, along with safety and efficacy. In this manner, device 10 may encourage more users to carry it, and thereby reduce the risks associated with anaphylactic shock, heart attack, exposure to toxic agents, and other conditions capable of treatment with one or more liquid medicaments carried by device 10.

Figure 2:
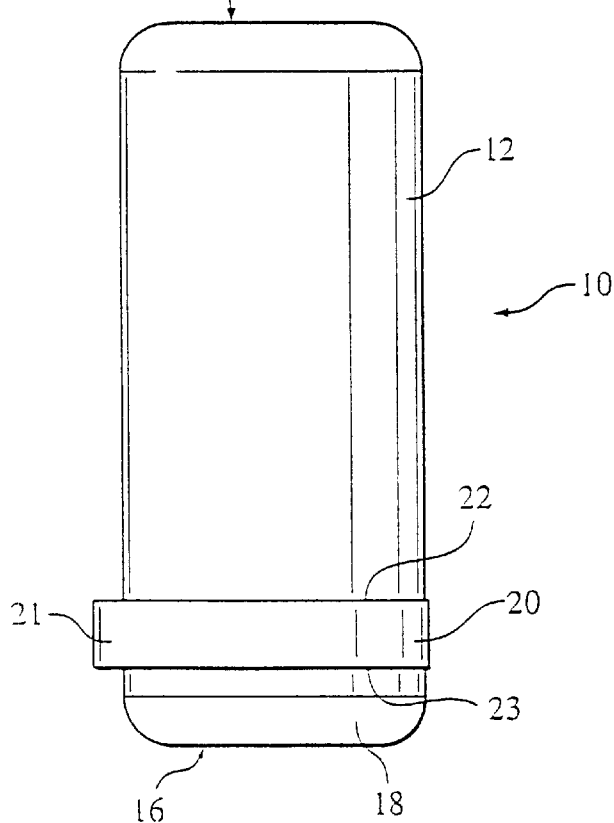
FIG. 2 is a side view of the device of FIG. 1.
Figure 3:
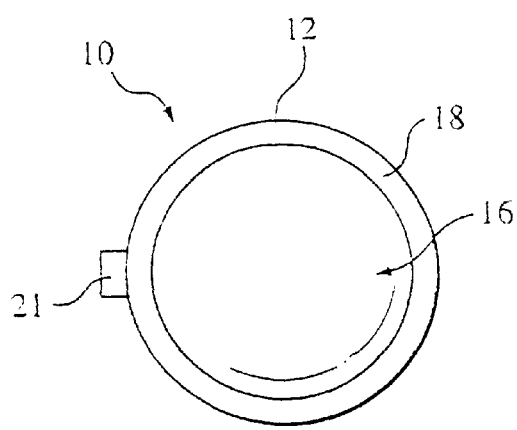
FIG. 3 is an end view of the device of FIG. 1.
Figure 4:
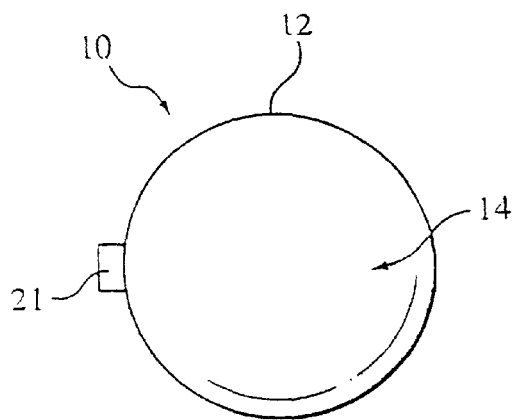
FIG. 4 is another end view of the device of FIG. 1.

FIGS. 2, 3, and 4 are side, first end, and second end views, respectively, of device 10 of FIG. 1. FIGS. 5–9 are various cross-sectional side views of device 10 during different stages of use. As shown in FIGS. 5–9, device 10 may include a reservoir 30, a needle 32, a piston member 34, a spring 36, a loading member 38, and a piston 44. Needle 32 is in fluid communication with reservoir 30, which contains a liquid medicament. In some embodiments, device 10 may include multiple reservoirs or sub-divided reservoirs that enable containment and automated injection of multiple liquid medicaments, if desired.

For anaphylactic shock, examples of suitable liquid medicaments contained in reservoir 30 include epinephrine and atropine. For heart attacks, anti-arrhythmic medicaments may be contained within reservoir 30. For exposure to toxic agents, a variety of liquid medicaments may be provided in reservoir 30. Conceivably, other liquid medicaments such as insulin could be provided for treatment of non-emergency conditions.

Needle 32 and spring 36 preferably are made of metal. The various components 30, 34, 38, 44 of device 10 can be constructed from durable plastics such as polyester. Piston member 34 and loading member 44 preferably are made from plastics that provide a moderate degree of flexibility and elasticity. Such materials may be selected in part on the basis of the suitability for recycling. Indeed, some of the components, such as housing 12, can be made from recycled materials. Reservoir 30 and needle 32, which contain and transport the liquid medicament, ordinarily will be manufactured from virgin materials due to sterility and biocompatibility concerns.

Reservoir 30 may be substantially cylindrical in shape, and may include a small needle aperture 40 at one end for receipt of needle 32. Needle 32 may be mounted in aperture 40 with a biocompatible sealant to prevent leakage of reservoir 30. Another end of reservoir 30 may define a larger aperture 42 for receipt of piston 44. A gasket 46 fills aperture 42, sealing it against leakage and contamination of the liquid medicament. Piston gasket 46 defines an aperture, however, for receipt of a shaft 48 forming part of piston 44. A first piston face 50 extends into reservoir 30, while a second piston face 52 resides outside of reservoir 30. Shaft 48 extends between piston faces 50, 52, and is translatable within the aperture defined by gasket 46. In this manner, first piston face 50 is movable to drive liquid medicament out of reservoir 30 and through needle 32 for injection into the user.

Piston 44 and reservoir 30 may be disposed within an inner chamber 54 defined by piston member 34. Piston member 34 acts as a carriage for travel of piston 44 and reservoir 30 within housing 12, as well as an actuator for the piston to expel liquid medicament from the reservoir. In some embodiments, piston member 34 and piston 44 may be integrally formed with one another, e.g., by molding. In the example illustrated in FIGS. 5–9, however, piston 44 and piston member 34 are separate components. Second piston face 52 bears against an inner wall of inner chamber 54 such that downward movement of piston member 34 urges piston 44 downward.

Housing 12 defines an outer chamber 56 sized to accommodate travel of piston member 34, spring 36 and loading member 38 along the length of device 10. Frictional engagement of the outer wall of reservoir 30 with the inner wall of inner chamber 54 serves to carry the reservoir along with piston member 34 as it travels upward and downward within outer chamber 56. Frictional engagement of shaft 48 of piston 44 serves to carry it along with reservoir 30, and hence piston member 34, when the piston member moves upward within outer chamber 56.

Housing 12 may have a unitary construction or, as shown in FIGS. 5–9, include two or more sub-sections 58, 60. Sub-sections 58, 60 can be coupled together by a number of techniques including adhesive bonds, ultrasonically welded bonds, threaded couplers, and frictional or snap-fit arrangements. Housing 12 can be sealed with epoxy or other adhesives to promote a substantially water-resistant seal, and ensure longevity and durability of the device. In the example of FIGS. 5–9, sub-section 60 includes a radial flange 62 that is snap-fit into a detent 64 in sub-section 58 to couple the sub-sections together. Sub-sections 58, 60 may have different cross-sectional dimensions, or different diameters in the embodiments in which they are circular in cross-section.

First sub-section 58 may include a substantially cylindrical retention ring 66 that extends downward from proximal end 14 and retains spring 36 against the inner wall of outer chamber 56. Retention ring 66 may be integrally molded with housing sub-section 58. One end of spring 36 bears against the interior of housing 12 at proximal end 14, while the other end bears against a flange 68 that extends radially outward from piston member. A portion of spring 36 may surround an upper portion 70 of piston member 34. In this manner, spring 36 is maintained in alignment relative to the inner wall of outer chamber 56 by retention ring 66 and upper portion 70 of piston member 34.

Loading member 38 can be constructed to include an outer wall that defines another inner chamber 72. A raised inner wall 74 may define both an aperture 76 for needle 32 and a stop surface 78 for reservoir 30. Needle 32 may reside within a protective sheath 79 prior to use. At least a portion of loading member 38 extends outward from distal end 18 of device 10 for engagement with an injection site, such as the user's thigh. Loading member 38 may have a flared lip 80 that flares radially outward. Flared lip 80 may engage a detent 82 defined by second sub-section 60 to retain loading member 38 within outer chamber 56 of housing 12. Flared lip 80 bears against a ramped lip 84 defined by piston member 34.

Figure 6:
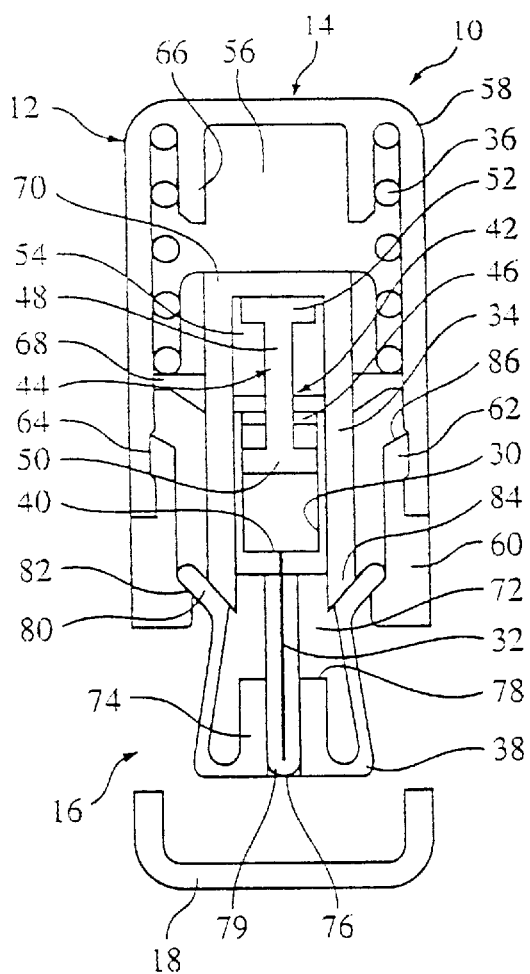
FIG. 6 is a cross-sectional side view of the device of FIG. 1 at a first stage of operation.
Figure 7:
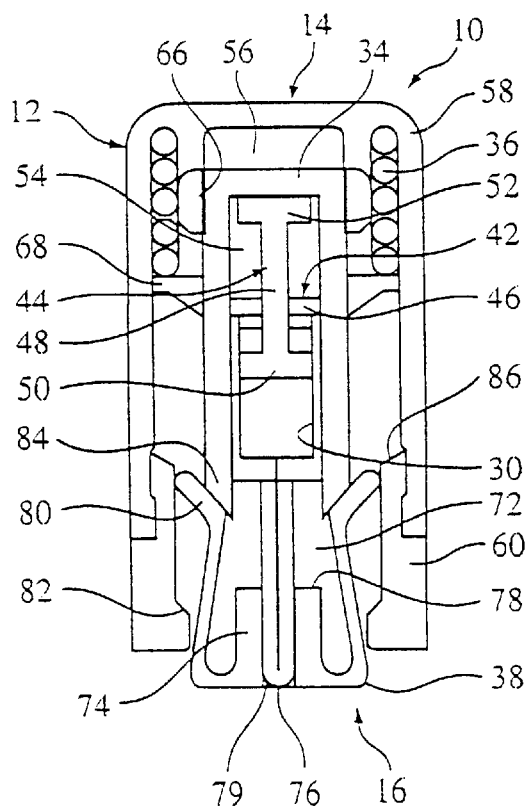
FIG. 7 is a cross-sectional side view of the device of FIG. 1 at a second stage of operation.

As shown in FIG. 6, cap 18 can be removed from housing 12 by tearing away strip 20. In this manner, loading member 38 is exposed at distal end 16 of device 10. Loading member 38 is movable upward against the bias produced by spring 36 to thereby load the spring and compress it, as shown in FIG. 7. Specifically, loading member 38 moves upward when the user applies the loading member to an injection site with sufficient force to overcome the spring bias. In this manner, flared lip 80 bears against ramped lip 84 of piston member 34 during upward movement of loading member 38 into outer chamber 56 of housing 12. With further reference to FIG. 7, flange 68 of piston member 34, in turn, bears against spring 36, compressing it against its intrinsic bias as the piston member travels upward.

Figure 8:
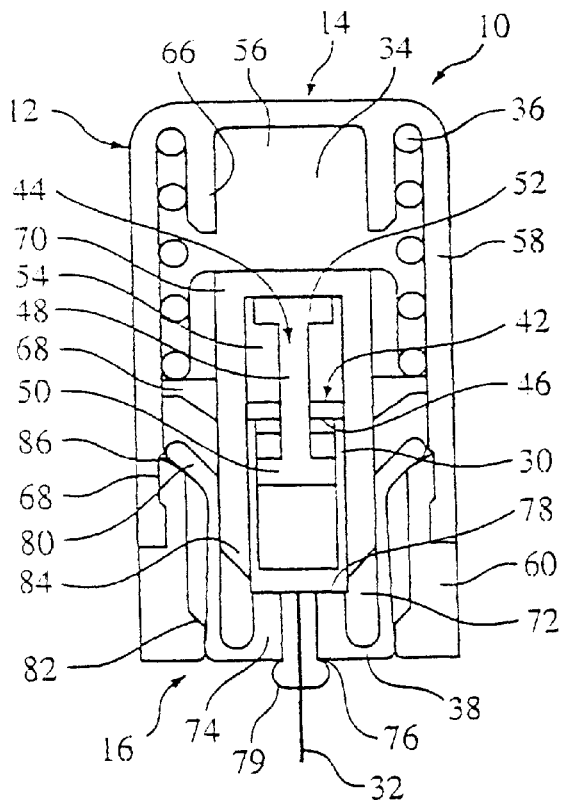
FIG. 8 is a cross-sectional side view of the device of FIG. 1 at a third stage of operation.

As shown in FIG. 8, flared lip 80 eventually extends upward above another detent 86 having a diameter that is greater than detent 82. Upon engagement with detent 86, flared lip 80 extends outward. Detent 86 prevents loading member 38 from moving downward and, in effect, locks the loading member into position. When flared lip 80 locks into detent 86 and spring 36 generates a sufficient level of spring force, loading member 38 permits the spring to expand downward toward the injection site. In particular, loading member 38 and piston member 34 are cooperatively arranged such that flared lip 80 defines an aperture that is initially sized smaller than piston member 34, but expands to permits downward movement of piston member 34, piston 44, reservoir 30, and needle 32 in response to expansion of spring 36.

Flared lip 80 is biased inward by the inner wall of second sub-section 60, which has a smaller diameter than first sub-section 58. Loading member 38 preferably is formed from a flexible and elastic material, however, and expands outward when it reaches detent 86, increasing the size of the aperture defined by the loading member. As mentioned above, loading member 38 can be constructed from a plastic material such as polyester that provides degrees of both flexibility and elasticity. The increased size permits piston member 34 to extend into inner chamber 72. When spring 36 reaches a sufficient level of spring force and flared lip 80 has reached detent 86, the spring exerts a bias back against piston member 34 that is sufficient to drive ramped lip 84 against the flared lip, driving piston member 34 into loading member 38. Thus, as shown in FIG. 8, loading member 38 is radially enlarged to permit receipt of a portion of piston member 34 within chamber 72.

Figure 9:
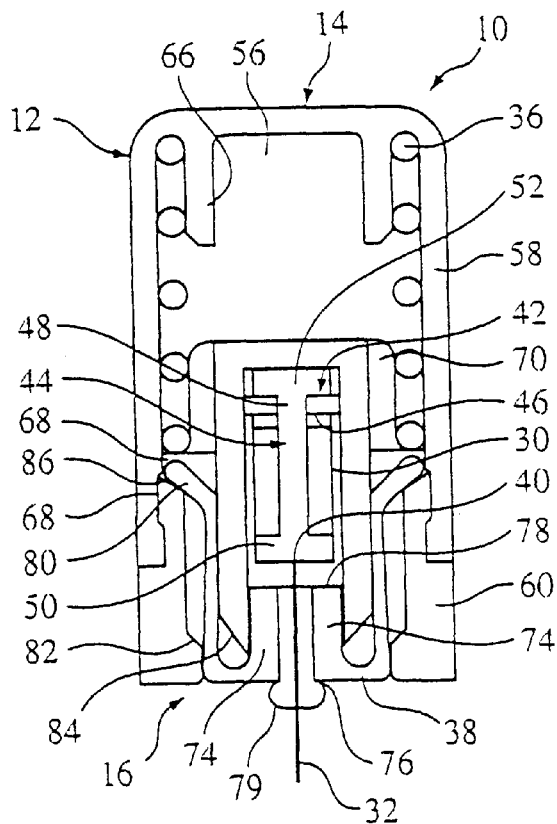
FIG. 9 is a cross-sectional side view of the device of FIG. 1 at a fourth stage of operation.

As spring 36 expands, it drives piston member 34, piston 44, and reservoir 30 downward together toward loading member 38. Following engagement with detent 86, loading member 38 may be substantially flush with the distal end 16 of device 10, as shown in FIGS. 8 and 9. As piston member 34 and reservoir 30 travel downward, as shown in FIG. 8, needle 32 is driven through protective sheath 79. Protective sheath 79 may be formed from a thin plastic or rubber material, such as polyester, polyurethane, silicone rubber, and the like. Needle 32 ruptures protective sheath 79 and is exposed for entry into the injection site, e.g., in the user's thigh. As shown in FIGS. 8 and 9, portions of piston member 34 and reservoir 30 enter chamber 72 of loading member 38 and continue to travel until the reservoir abuts the stop surface 78. At that point, the spring bias exerted by spring 36 on piston member 34 overcomes the frictional force exerted between reservoir 30 and the piston member.

As a result, as shown in FIG. 9, piston member 34 is able to continue travel downward into chamber 72 of loading member 38. Reservoir 30 stops traveling, however, and rests against stop surface 78. After reservoir 30 stops, piston 44 continues to travel with piston member 34, driving first piston face 50 through reservoir 30. First piston face 50 thereby expels the liquid contents of the reservoir through needle 32, which is lodged in the injection site. Needle 32 preferably is driven into the injection site under the initial spring force provided by spring 36, as shown in FIG. 8.

Insertion of needle 32 preferably requires no manual intervention by the user following the user's initial application of loading member 38 to the injection site. Rather, spring 36 expands with sufficient force to deploy needle 32 automatically following upward travel of loading member 38 to detent 86. Thus, the user simply drives loading member 38 against the injection site, forcing it into housing 12. This simple act by the user starts a chain reaction of events that causes compression and then expansion of spring 36 to drive needle into the injection site and expel the contents of reservoir 30. The relative simplicity of the interaction between loading member 38, piston member 34, piston 44, and reservoir 30 promotes reliability, which is a paramount concern given the application of device 10 to emergency medical conditions.

An automated injection device constructed in a manner similar to device 10 shown in FIGS. 1–9 may provide quick, convenient, and automated injection of liquid medicaments. In particular, operation of such a device 10 merely requires application of loading member 38 to the injection with sufficient force to drive the loading member upward into housing 12. From that point forward, the operation of spring 36, piston member 34, piston 44, reservoir 30, and needle 32 is automatic, and results in effective injection of the liquid medicament contained within the reservoir. As alternatives, an electrical or pneumatic actuation mechanism could be provided in lieu of spring 36. The arrangement of the inner components of device 10, i.e., piston member 34, piston 44, reservoir 30, needle 32, spring 36, and loading member 38 permits the device to be constructed at a reduced size.

Figure 5:
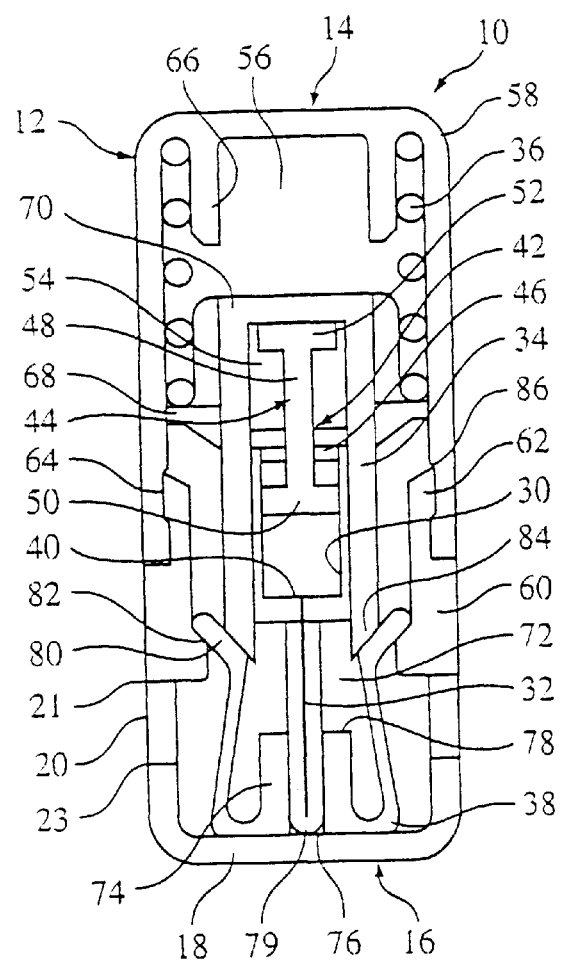
FIG. 5 is a cross-sectional side view of the device of FIG. 1.

In particular, such components are arranged to at least partially overlap along the length of device 10, in periods of use and nonuse, to restrict the longitudinal length of device 10. As shown in FIG. 5, for example, before device 10 is used, reservoir 30, piston 44, piston member 34, and spring 36 substantially overlap with one another and are coaxially aligned along the longitudinal axis of housing 12. As a result, the length of device 10 is reduced relative to arrangements in which such components would be disposed end-to-end within device housing 12. An arrangement as shown in FIG. 5 provides substantial reductions in length, while still providing automated convenience to the user. With reduced size, a user is more likely to carry device 10 and thereby more likely to survive a medical emergency that is treatable with the device.

With reference to FIG. 1, with the reduced size afforded by device 10, housing 12 and cap 18 together may have a length 24 in the range of approximately 2 to 3 inches and a diameter (or width 26 and depth 28 in the case of a rectangular cross-section) in the range of approximately 1 to 2 inches. In one particular embodiment, device 10 has a length in the range of approximately 2.5 to 3.0 inches and a diameter of approximately 1.0 to 1.5 inches. More particularly, a device 10 is envisioned having a length of approximately 2.75 inches and a diameter of approximately 1.25 inches, providing exceptional convenience and portability.

Figure 10:
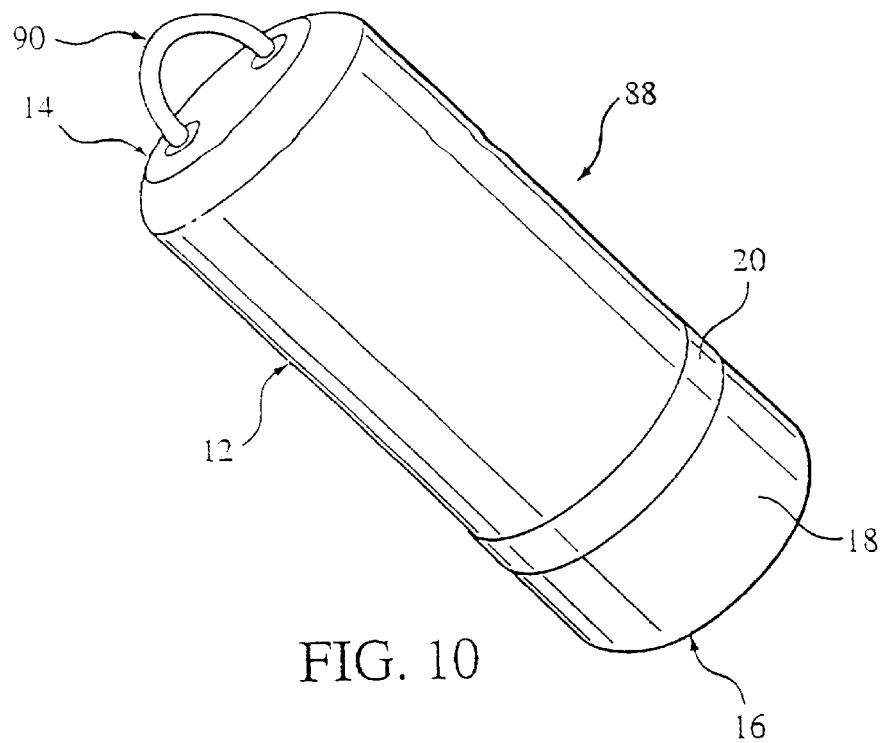
FIG. 10 is a conceptual view of a housing for a device as shown in FIG. 1.

FIGS. 10–13 are a conceptual view of housings for automated injection devices as shown in FIG. 1. Although device 10 is shown in FIGS. 1–9 as having a substantially cylindrical shape, it may be susceptible to a number of different configurations designed to maintain a reduced size and suit the needs of individual users. FIG. 10, for example, shows an automated injection device 88 that conforms substantially to device 10 of FIGS. 1–9, but is configured as a key fob device. In particular, device 88 includes an integrated ring 90 for receipt of keys or a keychain ring. Device 88 alternatively could be attached to a necklace or strap. As further alternatives, device 88 could be coupled to an ankle or wrist bracelet or a zipper fob. In this manner, the user may conveniently carry device 88 with his or her keys. Ring 90 may be integrally molded with housing 12, bonded to the housing via adhesives or ultrasonic welding, or snap-fit into holes in the housing. The size of device 88 may conform substantially to that of device 10 as described above with respect to FIG. 1.

Figure 11:
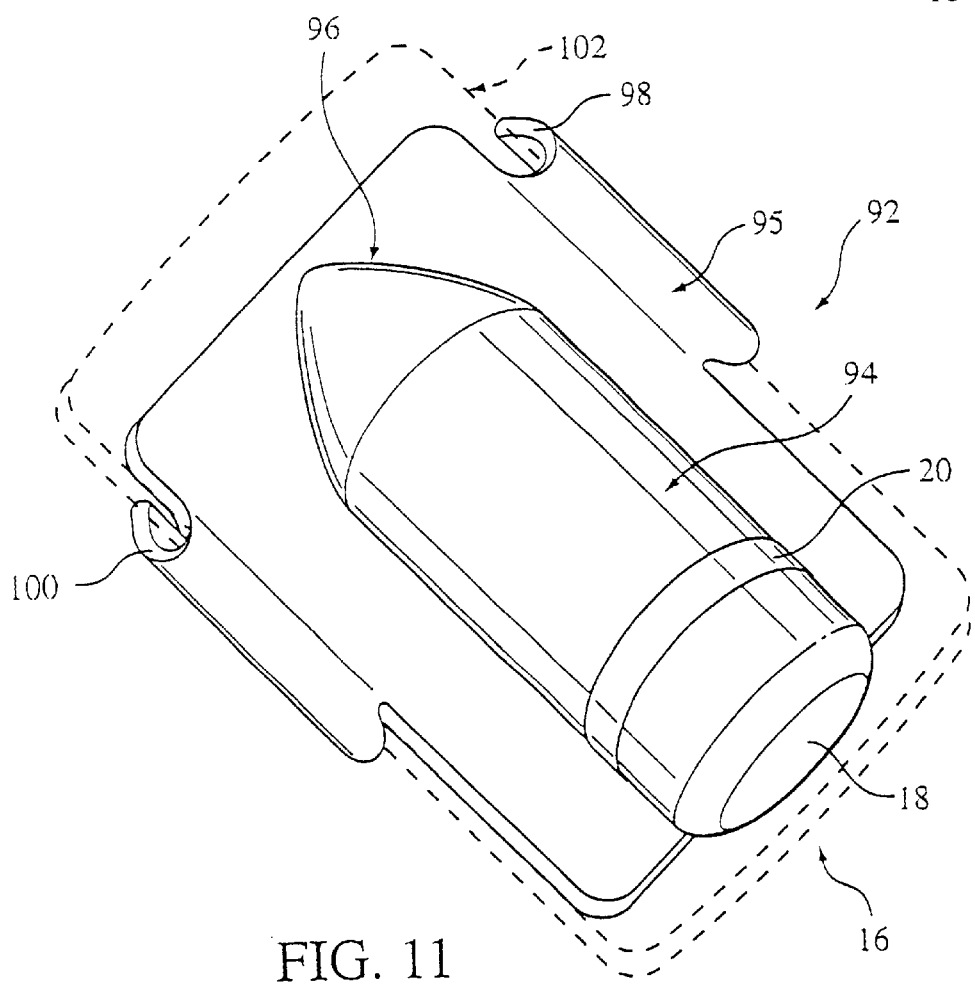
FIG. 11 is another conceptual view of another housing for a device as shown in FIG. 1.

FIG. 11 is another conceptual view of a housing for a device as shown in FIG. 1. Device 92 of FIG. 11 may having a housing 94 that is integrally molded with or attached to a platform 95. For example, housing 94 may taper upward and inward to merge with platform 95, as indicated by reference numeral 96. Platform 95 could be made substantially flat and planar and approximate the width of a credit card. In the embodiment of FIG. 11, platform 95 includes attachment wings 98, 100 that permit attachment of device 92 to another device carried by the user. For example, attachment wings 98, 100 can be formed from a flexible and somewhat elastic material, and configured to clip onto the sides of a PDA, e.g., a Palm or Windows CE device, or a mobile telephone, indicated by reference numeral 102 and drawn with dashed lines. In this manner, automated device 92 mounts onto the back of a device 102 that is already carried by the user, further promoting convenience and portability.

Figure 12:
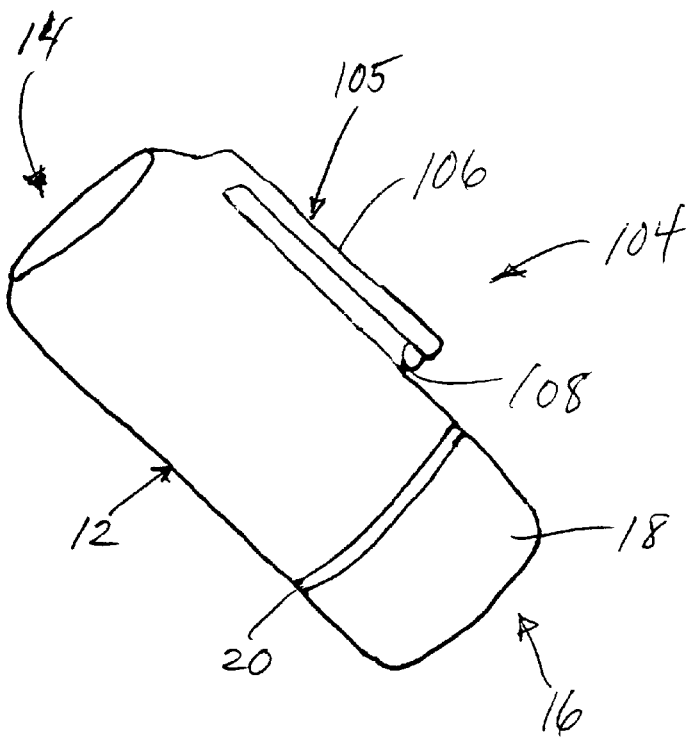
FIG. 12 is an additional conceptual view of another housing for a device as shown in FIG.1.

FIG. 12 is an additional conceptual view of a housing for an automated injection device as shown in FIG. 1. Automated injection device 104 of FIG. 12 conforms substantially to device 10 of FIGS. 1–9, but further includes an integrated clip 105 having an arm 106 and a spacer 108. Clip 105 operates like the clip on a pen, permitting device 104 to be clipped to and retained within a pocket or to another thin element that fits between the major portion of housing 12 and the clip. Clip 105 can be integrally molded with housing 12.

Figure 13:
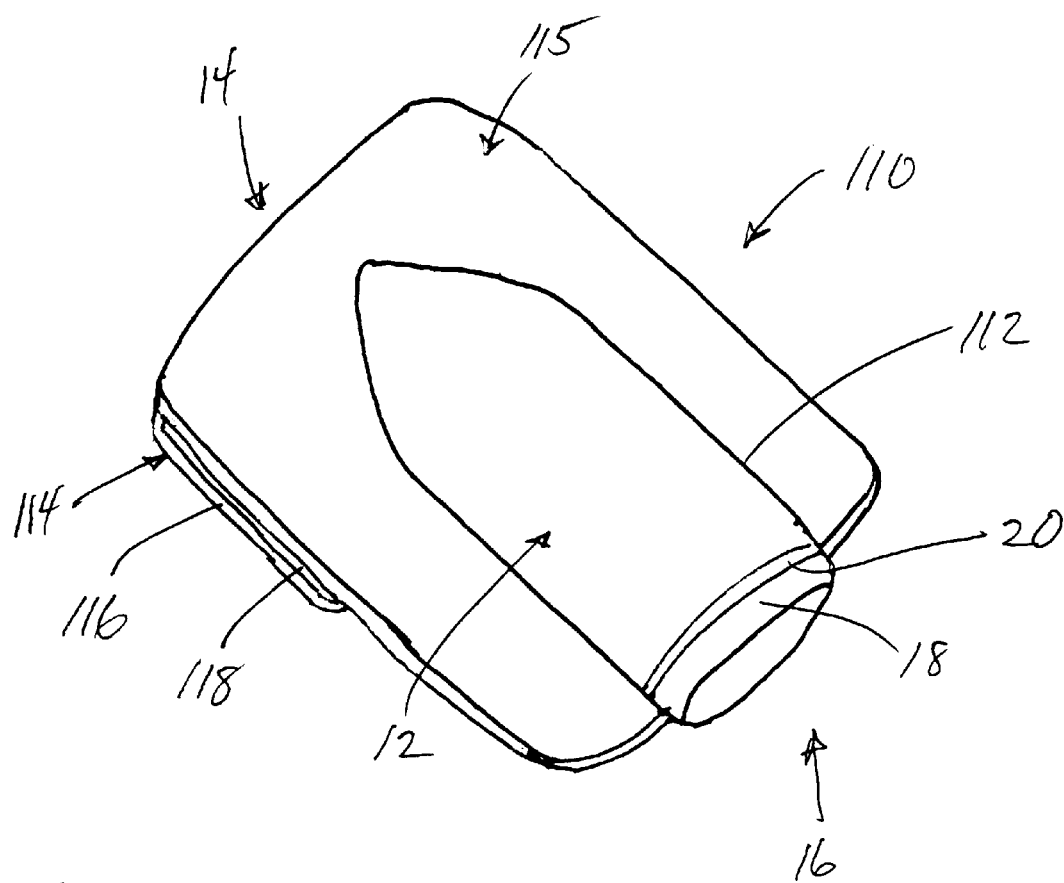
FIG. 13 is another conceptual view of an added housing for a device as shown in FIG. 1.

FIG. 13 is another conceptual view of a housing for an automated injection device as shown in FIG. 1. Automated injection device 110 of FIG. 13 conforms substantially to device 92 of FIG. 11. Instead of attachment wings 98, 100 for attachment to a device, however, device 110 includes a substantially planar clip 114 that extends outward from and substantially parallel to platform 115. Clip 114 can be integrally molded with platform 114, and may include planar arm 116 that extends along the width of the platform and defines a slot 118 for receipt of the flap of a pocket or some other thin element. Platform 115 may conform to the width of a credit card, and thereby promote convenience and portability for the user.

A number of embodiments of the invention have been described. Nevertheless, it will be understood that various modifications may be made without departing from the spirit and scope of the invention. Accordingly, other embodiments are within the scope of the following claims.

What is claimed is:

1. An automated injection device comprising:
    a reservoir;
    a needle in fluid communication with the reservoir;
    a piston member with a piston face positioned within the reservoir;
    a spring adjacent the piston member; and
    a loading member that is movable to compress the spring, the loading member permitting the spring to expand following compression, whereby the expanding spring drives the piston member such that the piston face moves within the reservoir and expels the contents of the reservoir through the needle.

2. The device of claim 1, wherein the loading member is oriented to drive the piston member to compress the spring, the loading member permitting movement of the piston member away from the spring after the spring has been compressed to a predetermined degree.

3. The device of claim 2, wherein the loading member has a flared lip that flares radially outward and defines an aperture that is initially sized smaller than the piston member such that the flared lip of the loading member bears against the piston member during compression of the spring, the flared lip extending outward as the spring reaches the predetermined degree of compression to thereby expand the aperture and permit receipt within the aperture of a portion of the piston member.

4. The device of claim 3, wherein the piston member defines a ramped lip for engagement with the flared lip.

5. The device of claim 3, further comprising a housing defining a channel having a narrowed portion and a widened portion for movement of the loading member, wherein the loading member includes an outer wall with a flared lip that extends radially outward and is generally biased inward by interaction with the narrowed portion of the channel, the flared lip extending outward upon movement of the ramped lip into the widened portion of the channel, thereby locking the loading member against a return into the narrowed portion of the channel after the spring is compressed.

6. The device of claim 2, wherein the piston member defines a channel and the reservoir is slidably mounted within the channel, the device further comprising a stop member that limits movement of the reservoir when the expanding spring drives the piston member such that continued movement of the piston member following abutment of the reservoir with the stop member causes the piston face to move through the reservoir and expel the contents of the reservoir through the needle.

7. The device of claim 6, wherein the stop member is formed within the aperture defined by the loading member.

8. The device of claim 7, wherein the aperture defines an annular recess that circumscribes a raised circular wall, the raised circular wall forming the stop member.

9. The device of claim 1, wherein the piston member defines a channel and the reservoir is slidably mounted within the channel, the device further comprising a stop member that limits movement of the reservoir when the expanding spring drives the piston member such that continued movement of the piston member following abutment of the reservoir with the stop member causes the piston face to move through the reservoir and expel the contents of the reservoir through the needle.

10. The device of claim 9, wherein the reservoir frictionally engages an inner surface of the channel and, upon abutment of the reservoir with the stop member, the spring force exerted on the piston member overcomes force generated by the frictional engagement of the reservoir and the inner surface of the channel to permit relative movement of the piston member and the reservoir.

11. The device of claim 1, wherein the injection needle is oriented to protrude through the loading member, the device further comprising a removable cap that covers a portion of the loading member.

12. The device of claim 1, wherein the loading member is oriented to compress the spring upon application of the loading member to a patient.

13. The device of claim 1, wherein the spring is normally in a substantially non-compressed state prior to movement of the loading member.

14. The device of claim 1, wherein a portion of the loading member extends outward from the device for engagement with the skin of a patient.

15. The device of claim 1, wherein the reservoir contains epinephrine.

16. The device of claim 1, wherein the reservoir and the needle are mounted to travel with the piston member to a limited extent.

17. The device of claim 16, further comprising a protective sheath that covers a portion of the needle, the needle puncturing the protective sheath when the expanding spring drives the piston member.

18. The device of claim 16, wherein the spring force generated by the spring is sufficient to drive the needle through the skin of a patient.

19. The device of claim 1, wherein the loading member, the spring, the piston member, and the reservoir are aligned along a common longitudinal axis, and portions of the loading member, the piston member, and the reservoir longitudinally overlap with one another during expansion of the spring.

20. The device of claim 1, wherein the device is less than approximately three inches in length, and less than approximately two inches in both width and in depth.

21. The device of claim 1, wherein the loading member and the piston member are formed from plastic materials.

22. The device of claim 1, wherein the device is less than approximately 3 inches in length, and less than approximately 2 inches in both width and in depth.

23. The device of claim 1, wherein the loading member and the piston member are formed from plastic materials.

24. An automated injection device comprising:
a housing having a first end and a second end, the housing defining an opening at the second end;
a piston member slidably mounted within the housing;
a reservoir slidably mounted within the piston member;
a needle in fluid communication with the reservoir;
a piston mounted within the piston member with a piston face positioned within the reservoir;
a spring that bears against the piston member on a side of the piston member adjacent the first end of the housing; and
a loading member oriented to drive the piston member toward the first end of the housing and thereby compress the spring, wherein the piston member and the loading member are configured to permit relative movement of the piston member and the loading member following compression of the spring, and the loading member defines a stop member that limits travel of the reservoir toward the second end of the chamber,
whereby the spring drives the piston member relative to the loading member and toward the second end of the housing, and the piston member drives the reservoir against the stop member such that continued movement of the piston member relative to the reservoir drives the piston face through the reservoir and expels the contents of the reservoir through the needle.

25. The device of claim 24, wherein the loading member has a flared lip that flares radially outward and defines an aperture that is initially sized smaller than the piston member such that the flared lip of the loading member bears against the piston member during compression of the spring, the flared lip extending radially outward as the spring reaches a predetermined degree of compression to thereby expand the aperture and permit receipt within the aperture of a portion of the piston member.

26. The device of claim 25, wherein the piston member defines a ramped lip for engagement with the flared lip.

27. The device of claim 25, wherein the aperture defines an annular recess that circumscribes a raised circular wall, the raised circular wall forming the stop member.

28. The device of claim 24, wherein the housing defines a channel having a narrowed portion and a widened portion for movement of the loading member, wherein the loading member includes an outer wall with a flared lip that extends radially outward and is generally biased inward by interaction with the narrowed portion of the channel, the flared lip extending outward upon movement of the flared lip into the widened portion of the channel, thereby locking the loading member against a return into the narrowed portion of the channel after the spring is compressed.

29. The device of claim 24, wherein the reservoir frictionally engages an inner surface of the channel within the piston member and, upon abutment of the reservoir with the stop member, the spring force exerted on the piston member overcomes force generated by the frictional engagement of the reservoir and the inner surface of the channel to permit relative movement of the piston member and the reservoir.

30. The device of claim 24, wherein the injection needle is oriented to protrude through the loading member, the device further comprising a removable cap that covers a portion of the loading member.

31. The device of claim 24, wherein the loading member is oriented to compress the spring upon application of the loading member to a patient.

32. The device of claim 24, wherein the spring is normally in a substantially non-compressed state prior to movement of the loading member.

33. The device of claim 24, wherein a portion of the loading member extends outward from the device for engagement with the skin of a patient.

34. The device of claim 24, wherein the reservoir contains epinephrine.

35. The device of claim 24, further comprising a protective sheath that covers a portion of the needle, the needle puncturing the protective sheath when the expanding spring drives the piston member.

36. The device of claim 24, wherein the spring force generated by the spring is sufficient to drive the needle through the skin of a patient.

37. The device of claim 24, wherein the loading member, the spring, the piston member, and the reservoir are aligned along a common longitudinal axis, and portions of the loading member, the piston member, and the reservoir longitudinally overlap with one another during expansion of the spring.

38. A method for injection of a liquid medicament using a device having a reservoir, a needle in fluid communication with the reservoir, a piston member with a piston face positioned within the reservoir, a spring that bears against the piston member, and a loading member oriented to drive the piston member to compress the spring, the piston member and the loading member being configured to permit relative movement when the compressed spring reaches a sufficient level of spring force, wherein a portion of the loading member extends outward from the device, the method comprising:
pushing the loading member against a patient to drive the loading member into the device and toward the piston member, thereby compressing the spring,
wherein the spring expands to drive the piston member relative to the loading member and extend the needle outward from the device and drive the piston face to expel the contents of the reservoir through the needle.

39. A method for injection of a liquid medicament using a device having a housing having a first end and a second end, the housing defining an opening at the second end, a piston member slidably mounted within the housing, a reservoir slidably mounted within the piston member, a needle in fluid communication with the reservoir, a piston mounted within the piston member with a piston face positioned within the reservoir, a spring that bears against the piston member on a side of the piston member adjacent the first end of the housing, and a loading member oriented to drive the piston member toward the first end of the housing and thereby compress the spring, wherein the piston member and the loading member are configured to permit relative movement when the compressed spring reaches a sufficient level of spring force, the loading member defines a stop member that limits travel of the reservoir toward the second end of the chamber, and a portion of the loading member extends outward from the opening, the method comprising:
pushing the loading member against a patient to drive the loading member into the device and toward the piston member, thereby compressing the spring,
wherein the spring expands to drive the piston member relative to the loading member and extend the needle outward from the opening and drive the piston face to expel the contents of the reservoir through the needle.

40. An automated injection device comprising:
a reservoir;
a needle in fluid communication with the reservoir;
a piston member with a piston face positioned within the reservoir;

a spring adjacent the piston member; and a loading member that is movable to compress the spring and permit the spring to expand following compression, the expanding spring driving the piston member such that the piston face moves within the reservoir and expels the contents of the reservoir through the needle, wherein the piston member and the reservoir partially overlap along a longitudinal extent of the device and are sized such that the device has a length of less than or equal to approximately 3.0 inches and a width of less than or equal to approximately 2.0 inches.

41. The device of claim 40, wherein the device has a length in the range of approximately 2.5 inches to 3.0 inches, and a width in the range of approximately 1.0 to 1.5 inches.

42. The device of claim 40, wherein the device has a length of approximately 2.75 inches, and a width of approximately 1.25 inches.

43. The device of claim 40, wherein the device is substantially cylindrical and the width corresponds to a diameter of the device.

44. The device of claim 40, further comprising a ring extending from the device for receipt of at least one of a keyring, a key, a necklace, a chain, and a strap.

45. The device of claim 40, further comprising a substantially planar platform coupled to the device, the platform including attachment wings for clipping the platform to another device.

46. The device of claim 45, wherein the other device is one of a PDA and a mobile telephone.

47. The device of claim 45, further comprising a substantially planar platform coupled to the device, the platform including a clip-like member for attachment of the platform to a thin sheet-like member.

* * * * *